United States Patent

Kormann et al.

[11] Patent Number: 5,929,260
[45] Date of Patent: Jul. 27, 1999

[54] HYDROGENATION USING MAGNETIC CATALYSTS

[75] Inventors: Claudius Kormann, Schifferstadt; Thomas Wettling, Limburgerhof; Ekkehard Schwab, Neustadt; Jochem Henkelmann, Mannheim, all of Germany

[73] Assignee: BASF Aktiengesellschaft, Ludwigshafen, Germany

[21] Appl. No.: 08/646,277

[22] PCT Filed: Nov. 11, 1994

[86] PCT No.: PCT/EP94/03747

§ 371 Date: May 16, 1996

§ 102(e) Date: May 16, 1996

[87] PCT Pub. No.: WO95/13874

PCT Pub. Date: May 26, 1995

[30] Foreign Application Priority Data

Nov. 16, 1993 [DE] Germany .............................. 43 39 139

[51] Int. Cl.⁶ .................................................. C07D 301/00
[52] U.S. Cl. .............................................................. 549/540
[58] Field of Search ...................... 502/240, 258, 502/261, 262, 332, 300, 325, 326; 428/694 BY, 694 BA, 403, 900, 407; 549/540; 252/62.54, 62.51 C, 62.56

[56] References Cited

U.S. PATENT DOCUMENTS

| Re. 29,419 | 9/1977 | DeCraene | 502/326 X |
|---|---|---|---|
| 3,228,881 | 1/1966 | Thomas | 252/62.54 |
| 4,201,827 | 5/1980 | Heitkamp | 428/283 |
| 4,247,987 | 2/1981 | Coulaloglou et al. | 34/1 |
| 4,309,290 | 1/1982 | Heitkamp | 210/695 |
| 4,382,982 | 5/1983 | Whillans | 427/130 |
| 4,847,394 | 7/1989 | Schuster | 549/540 |
| 5,128,204 | 7/1992 | Charmot | 420/329 |
| 5,172,842 | 12/1992 | Viscio et al. | 225/93 |
| 5,217,810 | 6/1993 | Lehner et al. | 428/403 |

FOREIGN PATENT DOCUMENTS

| 21 854 | 1/1981 | European Pat. Off. . |
| 27 640 | 4/1981 | European Pat. Off. . |
| 115 684 | 8/1984 | European Pat. Off. . |
| 125 995 | 11/1984 | European Pat. Off. . |
| 402 743 | 12/1990 | European Pat. Off. . |
| 26 24 873 | 6/1989 | France . |
| 36 19 746 | 12/1987 | Germany . |

OTHER PUBLICATIONS

Journal of Magnetism and Magnetic Materials, vol. 83, 1990—pp. 285–289 (no month).

*Primary Examiner*—Michael Lewis
*Assistant Examiner*—Stuart L. Hendrickson
*Attorney, Agent, or Firm*—Keil & Weinkauf

[57] ABSTRACT

Catalysts are composed of
a) a magnetizable core,
b) which may be coated with a binder and
c) which carries catalytically active metals or metal compounds on its surface.

3 Claims, No Drawings

HYDROGENATION USING MAGNETIC CATALYSTS

BACKGROUND OF THE INVENTION

1. Field of the Invention

The present invention relates to catalysts composed of
a) a magnetizable core having a diameter of from 5 to 100 nm,
b) which may be coated with a binder and
c) which carries catalytically active metals or metal compounds on its surface.

The present invention furthermore relates to a process for the preparation of these catalysts, their use and a method for removing these catalysts from reaction solutions.

2. Description of the Related Art

Reactions in solution with homogeneous or suspended catalysts are widely encountered in the chemical industry. However, the removal and, if required, recycling of these catalysts presents difficulties in many cases. If catalysts dissolved in the reaction solution, ie. homogeneous catalysts, are used, the products are usually separated from the catalysts by distillation and the catalysts remain in the bottom product of the distillation. The catalysts are frequently deactivated during this procedure and can be reused only after being worked up by a complicated process. In the case of thermally unstable products, this method of removal by distillation leads to a deterioration in the product quality owing to decomposition reactions. In these cases, the catalyst may alternatively be removed, for example, by extraction or by adsorption, for example on active carbon. Attempts have also been made to achieve separability of product and catalyst by heterogenization, ie. by binding the catalysts to finely divided substances which are insoluble in the reaction mixture. However, the filterability of such heterogenized catalysts is often poor.

In the case of suspension catalysts, the highest catalytic activity is frequently achieved with small catalyst particles having a high specific surface area. Owing to the particle size, these particles, too, are difficult to remove from the reaction mixture by simple filtration, so that the technically complicated separation methods described above have to be used.

A possible method for removing metallic suspension catalysts containing the magnetic elements iron, cobalt and nickel entails removal in a magnetic field (magnetic filter) (Journal of Magnetism and Magnetic Materials 85 (1990), 285). However, this method is limited to magnetic metals and, in the case of larger particles, also has the difficulty that the particles agglomerate to form larger particles as a result of permanent magnetization.

The immobilization of enzymes by binding to magnetic particles is described, for example, in EP-A 125995. However, the use of these enzymes is limited to mild reaction conditions under which the enzymes bound in this manner are chemically stable.

SUMMARY OF THE INVENTION

EP-A 21 854 describes magnetic catalyst particles having a size of about 800 μm for a fluidized-bed process for a reformer process. The catalytically active metal compounds such as hexachloroplatinic acid can be applied, for example by impregnation, to spray-dried mixtures of $Al_2O_3$ and stainless steel.

EP-A 115 684 concerns magnetizable iron particles having a size of from 150 to 300 μm which can be used, without application of a coating or being silvercoated, for catalysis in fluidized beds.

DESCRIPTION OF THE PREFERRED EMBODIMENTS

It is an object of the present invention to provide metal-containing catalysts for liquid-phase reactions, which catalysts can be removed from the reaction mixture in a technically simple manner.

We have found that this object is achieved by the catalysts described above. We have furthermore found a process for their preparation, their use and a method for removing these catalysts from reaction mixtures.

The core of the novel catalysts consists of a magnetizable particle. Magnetizable particles are to be understood as being those particles which are magnetic in an external magnetic field. In general, such substances have a saturation magnetization of from 20 to 200, preferably from 30 to 100, $nTm^3/g$. The size of the magnetizable particles can be chosen within wide limits. If, however, permanent magnetization of these particles by an external magnetic field is to be avoided, particles having a diameter of from 5 to 100 nm are used. The size of particles having such diameters is determined by known methods, for example by electron microscopy procedures, the values being average values for the particular sample.

Specifically, the following substances are suitable as magnetizable cores:

Iron, nickel, cobalt, chromium dioxide, iron oxides and cubic and hexagonal ferrites, such as ferrites doped with manganese, zinc and cobalt ions and with magnesium, calcium, strontium and barium ions. Such substances are obtainable in a manner known per se, for example by precipitation reactions of corresponding metal salts. Thus, magnetite $Fe_3O_4$ can be prepared from solutions of $Fe^{2+}/Fe^{3+}$ chlorides by precipitation with sodium hydroxide solution (cf. for example DE-A 36 19 746) and chromium dioxide by hydrothermal synthesis (cf. for example EP-A 27 640). The metallic cores can be prepared by thermal decomposition of metal carbonyls (cf. for example U.S. Pat. No. 3,228,881). Preferred substances for the magnetizable cores are magnetite, $\gamma$-$Fe_2O_3$, chromium dioxide and manganese zinc ferrite.

Depending on their diameters, which as a rule are small, the magnetizable cores generally have surface areas (determined according to DIN 66 132) of from 1 to 300 $m^2/g$.

The magnetizable cores can be reacted directly with metal compounds which bind by adsorption or chemically to the surface of the core. However, the magnetic core is preferably first coated with a binder. This binder should bind by adsorption or chemically to the magnetizable core and at the same time make it possible to bind, by adsorption or chemically, metal compounds which are catalytically active either directly or, if required, after chemical modification.

Preferred novel binders are organic polymers which are water-soluble or water-dispersible, ie. in general at least 1 g can be dissolved or dispersed in 1 l of water. Examples of monomers for Such polymeric binders are olefinically unsaturated compounds containing acid groups, such as unsaturated carboxylic acids, eg. acrylic acid or methacrylic acid, unsaturated sulfonic acids, eg. vinylsulfonic acid, and unsaturated phosphonic acids, such as vinylphosphonic acid, as well as unsaturated anhydrides, such as maleic anhydride, amino-carrying monomers, such as vinylamine, amido-carrying monomers, such as acrylamide, and vinylpyrrolidine, vinylpyrrolidone, vinylpyridine and vinylbipyridyl. Homo- and copolymers of the stated monomers may also be used. The polymers may contain further copolymerizable monomers, but the amount of the stated monomers is preferably at least 50% by weight. Homo- or copolymers of these compounds are commercially available or are obtainable, for example, by free radical polymerization. Polyesters, such as polylactide, are also suitable binders.

Polyacrylic acids having an average molecular weight of from 1000 to 1000000 are preferred. Polymers which contain up to 20% by weight of further monomers in addition to acrylic acid are also suitable. Such products are commercially available.

The amount of the binder is as a rule such that at least one monolayer of the binder can form on the magnetizable core. In general, from 0.1 to 5 mg, preferably from 0.3 to 1.5 mg, of polymer per $m^2$ of specific surface area of the magnetizable core are required.

In order to coat the magnetizable core with a binder, a solution of the binder in a polar solvent, such as water, may be added to the magnetizable material in a polar solvent, such as water. The temperature is, as a rule, from 10 to 100° C. The components are generally stirred for from 10 to 60 minutes, and the solid thus obtained is isolated, for example by filtration or by applying a magnetic field, and, if required, is dried. It may be isolated and the content of bound polymer may be determined by elemental analysis.

It is furthermore possible further to treat the resulting solids in a manner such that reactive groups which are present in the polymer are subjected to a reaction. For example, polar carboxyl groups may be liberated from ester groups present in the binder in a conventional manner by hydrolysis with a mineral base.

The novel catalysts carry metals or metal compounds on their surface. These are preferably the platinum metals, ruthenium, rhodium, palladium, osmium, iridium and platinum, or copper, silver, gold and rhenium, or compounds of these metals. Ruthenium, palladium and platinum are particularly preferred. For the preparation of the novel catalysts, metal compounds which are dissolved or finely suspended in a polar solvent may be bound chemically or adsorptively to the magnetizable cores, which, if required, are coated with a binder. These metal compounds are, for example, salts of the metals, such as acetates and nitrates. Examples are ruthenium chloride trihydrate, ruthenium oxide hydrate, palladium acetate, palladium chloride, rhodium chloride, platinum chloride, gold chloride, osmium tetraoxide, copper chloride, copper nitrate, silver nitrate and rhenium chloride. The solvents comprise $C_1$–$C_4$-alcohols, such as methanol, ethanol, isopropanol and tert-butanol, ethers, such as tetrahydrofuran, water, pyridine or mixtures of these solvents, preferably water. Depending on the polar groups present in the binder, the metal compounds may be bound by interactions with, for example, carboxyl groups, amino groups or oxo groups. In the case of (colloidal metal compounds,) such as ruthenium oxide hydrate, adsorptive binding may be effected. As a rule, from 0.1 to 20% by weight, based on the magnetizable core, of the metal compound in solution are reacted with the magnetic particles which may carry a binder. In general, the reaction is carried out at room temperature but may also be effected at from 0 to 100° C. It is complete as a rule after from 1 to 6 hours.

The products thus obtained can be used directly in solution as catalysts but may first be isolated, if necessary purified and then added to the reaction to be catalyzed.

The novel catalysts permit the catalysis of a large number of different reactions, for example hydrogenation of aromatic nuclei in the presence of further reducible groups using ruthenium-containing catalysts, hydroformylation of olefins using rhodium-containing catalysts, transvinylidations of vinyl ethers using palladium-containing catalysts and selective hydrogenation of carbon-carbon triple bonds to double bonds using palladium-containing catalysts.

The catalysts may be used in general at up to 250° C., and the reactions may be carried out at any pressure. The novel catalysts can be separated from the reaction mixtures by a magnetic filter, as described, for example, in Journal of Magnetism and Magnetic Materials 85 (1990) 285. A simple bar magnet has proven useful for separating off small amounts of the catalyst.

The novel catalysts furthermore have the advantage that, after removal of the magnetic field used for separation, they are not permanently magnetic and therefore do not agglomerate. This considerably facilitates the recycling of the catalysts to the reaction and their uniform distribution in the reaction mixture.

EXAMPLES

Preparation of the Magnetizable Particles 1.1 Magnetite $Fe_3O_4$ was prepared as follows The magnetite was prepared according to DE-A 35 00 471 by a precipitation reaction, by adding a stoichiometric solution of $Fe(^{2+})/Fe(^{3+})$ chlorides in water dropwise to a solution of sodium hydroxide in water. The precipitated magnetite was filtered off and washed chloride-free. A filter cake having a magnetite content of 26% by weight was formed. The dried pigment was characterized by the following measured values: The specific BET surface area was measured according to DIN 66 132. It was 51 $m^2/g$. The magnetic properties were determined using a vibrating sample magnetometer. The saturation magnetization was 85 $nTm^3/g$.

1.2 Preparation of Ruthenium Oxide Hydrate as a Catalytically Active Metal Compound The reaction was carried out according to Example 1 of DE-A 2132547. The ruthenium oxide hydrate was used in the form of a moist filter cake containing 8.4% by weight of ruthenium, for the following experiments:

1.3 Preparation of the Novel Catalyst 230 g of filter cake containing 60 g of the magnetizable particles prepared according to Example 1.1 and 71.3 g of the filter cake prepared according to Example 1.2 were dispersed in 200 g of water in the course of 15 minutes by vigorous stirring. A solution of 1.8 g of polyacrylic acid having an average molecular weight of 250,000 was then added to 3.3 g of water. The pH was brought to 7.9 by adding 13.4 g of a 5% strength by weight sodium hydroxide solution. After 15 minutes, the solid was filtered off and washed chloride-free with water. The filter cake was then washed with tetrahydrofuran THF and the water was substantially exchanged for THF. The filter cake thus obtained was characterized as follows: Ruthenium content: 2.1% by weight. Solids content (determined by drying at 70° C. under reduced pressure): 22% by weight, BET surface area 86 $m^2/g$.

1.4 Testing of the Catalytic Properties

In an autoclave, 70 g of bisphenol F bisglycidyl ether (prepared by condensation of formaldehyde and 2 equivalents of phenol and subsequent reaction with epichlorohydrin) and 10 g of the ruthenium magnetite suspension obtained according to Example 1.3 (corresponding to 3 o/oo by weight, based on the bisglycidyl ether, of Ru) were made up to a total weight of 150 g with THF. Heating was then carried out to 50–67° C. at a hydrogen pressure of 100 bar in the course of 7 hours. The total conversion was 94%. The epoxide equivalent value was 192.

This value corresponds to epoxide equivalent values as obtainable according to the prior art, for example EP-A 402 743.

The catalyst could be readily and completely separated from the reaction mixture by means of a magnet.

We claim:

1. A process for hydrogenating ring atoms of bisglycidyl ethers, containing aromatic rings, which process comprises hydrogenating the bisglycidyl ethers containing aromatic rings in the presence of a hydrogenation catalyst which comprises:

a) a magnetizable core having a diameter of from 5 to 100 nm, the magnetizable core being composed of a member selected from the group consisting of iron oxide, chromium dioxide, and manganese zinc ferrite;

b) a binder, coating the magnetizable core; and c) a catalytically active component, which is a metal or a compound of a metal selected from the group consisting of platinum group metals, copper, silver, gold, and rhenium, the catalytically active component being bound to the binder.

2. The process of claim 1, wherein the catalytically active component of the hydrogenation catalyst is ruthenium oxide hydrate.

3. The process of claim 2, wherein the binder coating the magnetizable core of the hydrogenation catalyst is a polyacrylic acid having an average molecular weight of from 1,000 to 1,000,000.

* * * * *